(12) United States Patent
Dittmer et al.

(10) Patent No.: US 8,217,647 B2
(45) Date of Patent: Jul. 10, 2012

(54) MEASURING AGGLUTINATION PARAMETERS

(75) Inventors: Wendy Uyen Dittmer, Eindhoven (NL); Peggy De Kievit, Eindhoven (NL); Jeroen Hans Nieuwenhuis, Eindhoven (NL); Menno Willem Jose Prins, Eindhoven (NL); Leonardus Josephus Van Ijzendoorn, Eindhoven (NL); Xander Jozef Antoine Janssen, Neerpelt (BE)

(73) Assignee: Koninklijke Philips Electronics N.V., Eindhoven (NL)

( * ) Notice: Subject to any disclaimer, the term of this patent is extended or adjusted under 35 U.S.C. 154(b) by 498 days.

(21) Appl. No.: 12/518,895

(22) PCT Filed: Dec. 18, 2007

(86) PCT No.: PCT/IB2007/055195
§ 371 (c)(1),
(2), (4) Date: Jun. 12, 2009

(87) PCT Pub. No.: WO2008/075285
PCT Pub. Date: Jun. 26, 2008

(65) Prior Publication Data
US 2010/0033158 A1    Feb. 11, 2010

(30) Foreign Application Priority Data

Dec. 19, 2006 (EP) .................................... 06126507
Sep. 21, 2007 (EP) .................................... 07116951

(51) Int. Cl.
*G01R 33/00* (2006.01)
*G01N 33/553* (2006.01)

(52) U.S. Cl. ........ 324/260; 324/262; 436/526; 436/806; 435/287.1

(58) Field of Classification Search .................. 324/260, 324/262; 435/287.1; 436/526, 806
See application file for complete search history.

(56) References Cited

U.S. PATENT DOCUMENTS

| 6,437,563 B1 | 8/2002 | Simmonds |
| 6,518,747 B2 | 2/2003 | Sager |
| 6,927,570 B2 | 8/2005 | Simmonds |
| 2003/0124745 A1 | 7/2003 | Chen |
| 2007/0172890 A1* | 7/2007 | Prins et al. ..................... 435/7.1 |

FOREIGN PATENT DOCUMENTS

| WO | 03050298 A1 | 6/2003 |
| WO | 2005010542 A2 | 2/2005 |
| WO | 2005010543 A1 | 2/2005 |
| WO | 2005111596 A1 | 11/2005 |
| WO | 2006056579 A2 | 6/2006 |

* cited by examiner

*Primary Examiner* — Reena Aurora

(57) ABSTRACT

A method and system for measuring agglutination in a target-induced agglutination assay with one or more magnetic particles is performed in a reaction chamber. After the magnetic particles, which are capable of binding to a target are provided in the assay, an agglutination process is performed resulting in agglutinated particles. Further an alternating current magnetic field ($H_{AC}$) is applied to the assay. The method further includes measuring an effect of the $H_{AC}$ on the one or more magnetic particles unattached to any surface. The measured effect is indicative of one or more agglutination parameters.

20 Claims, 12 Drawing Sheets

US 8,217,647 B2

MEASURING AGGLUTINATION PARAMETERS

FIELD OF THE INVENTION

The present invention relates to the field of biological, chemical or biochemical sensing. More particularly, the present invention relates to a method for quantitatively measuring one or more agglutination parameters of magnetic labels in a target-induced agglutination assay. The invention also relates to a corresponding kit, and a corresponding device.

BACKGROUND OF THE INVENTION

Recent efforts have been given to measurement techniques for determining the presence, and possibly the level of concentration, of targets in a larger mixture or solution in which the particles reside. It is often desirable to measure relatively low concentrations of certain organic compounds. In medicine, for example, it is very useful to determine the concentration of a given kind of molecule, usually in solution, which either exists naturally in physiological fluids e.g. blood or urine or which is introduced into the living system e.g. drugs.

One broad approach used to detect the presence of a particular compound of interest is the immunoassay technique, in which detection of a given molecular species, referred to generally as the ligand, is accomplished through the use of a second molecular species, often called the antiligand or the receptor, which specifically binds to the ligand of interest. The presence of the ligand of interest is detected by measuring, or inferring, either directly or indirectly, the extent of binding of ligand to antiligand e.g. by optical methods. A ligand can be considered a target or an analyte.

There are a number of immunoassay formats. All involve bindings but not all involve agglutination. In the non-agglutinating case, one label is generally attached to one target. Agglutination assays are rapid and easy to detect, and they are used when easy detection and immediate results are required e.g. in the field.

Quantitative tests based on optical detection of large particles are only moderately sensitive because they rely on measurements of turbidity (transmitted light through sample) or nephelometry (scattered light through sample), both of which are influenced by background interference from particulate matter. Consequently, optical methods are not suitable for use with raw samples such as whole blood, which contains cells, and saliva, which may have food particles.

Instead, magnetic particles made from magnetite and inert matrix material has long been used in the field of biochemistry. They range in size from a few nanometers up to a few microns in diameter and may contain from 15% to 100% magnetite. They are often described as superparamagnetic particles or, in the larger size range, as magnetic beads. The usual methodology is to coat the surface of the particles with some biologically active material which will cause them to bind strongly with specific microscopic objects or particles of interest e.g. proteins, viruses, cells, or DNA fragments. The magnetic particles may be considered as "handles" by which the objects can be moved or immobilized using a magnetic gradient, usually provided by a strong permanent magnet.

Previously, such magnetic particles have been used primarily for immobilizing the bound objects, but recent work has been done on using the particles as tags for detecting the presence of the bound complexes. Historically the detection and quantification of the bound complexes have been accomplished by means of radioactive, fluorescent, or phosphorescent molecules which are bound to the complexes of interest. However, these prior tagging techniques have various well-known disadvantages.

On the other hand, since the signal from a tiny volume of magnetic particles is exceedingly small, it has been natural that researchers have tried building detectors based on Superconducting Quantum Interference Devices (SQUIDs), which are well known to be the most sensitive detectors of magnetic fields for many applications. However, SQUIDs are quite sensitive measurement devices, but suffer inter alia from the disadvantage that the devices have to be cooled around cryogenic temperatures.

Recently, improved magnetic particle sensor devices have been disclosed by the present applicant, in particular in international patent applications WO 2005/010542 and WO 2005/010543, which are both hereby incorporated by reference in their entirety. These magnetic particle sensor devices have the advantages that measurement can be performed at around room temperature while at the same time having a sufficiently high signal-to-noise ratio (SNR).

U.S. Pat. No. 6,437,563 (to Simmonds et al. and Quantum Design, Inc.) recently disclosed an apparatus, which is provided for quantitatively measuring combinations of magnetic particles combined with analytes whose amount or other characteristic quality is to be determined. The magnetic particles are complexed with the analytes to be determined and are excited in a magnetic field of several hundred kHz. The magnetizations of the magnetic particles are thereby caused to oscillate at the excitation frequency in the manner of a dipole to create their own fields. These fields are inductively coupled to at least one sensor such as sensing coils fabricated in a gradiometer configuration. The output signals from the sensing coils are appropriately amplified and processed to provide useful output indications for combinations or agglutination of magnetic particles. However, working in the kiloHertz regime of oscillation may introduce unnecessary noise contributions, and additionally the application of a moving, in particular rotating, sample holder complicates the design as the rotating sample holder has to be relatively precise when the rotation is applied for decoupling of measurement and excitation. Additionally, the rotating sample holder does not easily facilitate sample manipulation immediately prior to, during, or immediately after magnetic measurement. Moreover, the coil technology applied by Simmonds et al. is not very sensitive, and thus relatively large amount of magnetic material is required for detection, which therefore increases the need for higher sample volumes. Finally, Simmonds et al. only measures the total amount of magnetic material both in the form of clusters and single particles, and effectively they do not distinguish between the two forms making it impossible to measure agglutination parameters.

It is also known that magnetic particles can rotate in a rotating magnetic field up to a certain frequency, the so-called critical slipping frequency. Above the critical slipping frequency the physical rotation of the magnetic particle cannot follow the rotations of the applied magnetic field.

Although a number of techniques for measuring of agglutination parameters exist, there is need for a more efficient and/or more reliable and/or more sensitive method. For example, it is a challenge in agglutination assays to detect a low number of clustered species in a background of many un-clustered species, and/or to detect a low number of un-clustered species in a background of many clustered species.

SUMMARY OF THE INVENTION

It is an object of the present invention to provide good methods and systems for measuring agglutination parameters. It is an advantage of embodiments according to the present invention that these mitigate, alleviate or eliminate one or more of the above mentioned disadvantages of the prior art singly or in any combination. The above objective is accomplished by a method and device according to the present invention.

The present invention provides a method for measuring agglutination of one or more particles in a target-induced agglutination assay performed in a reaction chamber, the method comprising the steps of providing magnetic particles in an assay, said magnetic particles being capable of binding to a target, performing an agglutination process resulting in agglutinated particles, the agglutinated particles comprising a least one of said magnetic particles. The method further comprises applying an alternating current magnetic field ($H_{AC}$) to the assay in the reaction chamber, and measuring with said at least one sensor element, an effect of the $H_{AC}$ on the one or more magnetic particles unattached to any surface of the reaction chamber, wherein the measured effect is indicative of one or more agglutination parameters. It is an advantage of embodiments according to the present invention that a high throughput can be obtained. It is an advantage of embodiments according to the present invention that a high sensitivity can be obtained. It is an advantage of embodiments according to the present invention that non-specific formation of clusters can be minimized. The assay, or the reaction chamber wherein the assay may be kept may be in the vicinity of the sensor element. The magnetic particles can be detected directly by the sensing method, or the particles can be further processed prior to detection. An example of further processing is that materials are added or that the (bio) chemical or physical properties of the particle are modified to facilitate detection.

The method further may comprise the step of concentrating magnetic particles near a sensor surface. The concentrating may be performed by attracting magnetic particles to a sensor surface in the form of chains. Detection thereof may be performed by applying a rotating field and identifying the rotating clusters, e.g. by optical imaging.

The method further may comprise the step of performing a separation process in dependency on the size of the agglutinated particles. It is an advantage of embodiments according to the present invention that the characterization of particles can be done for different sizes separately, thus reducing or avoiding influencing of the cluster size on the assay and thus providing an improved accuracy. It is an advantage of embodiments according to the present invention that a plurality of sensor elements may be arranged with each element having a sensor surface in the proximity of the assay, to provide quantitative agglutination parameters resulting from the separation process according to an embodiment of the present invention. In particular, a plurality of sensors may be arranged in relation to the agglutination assay for measuring different size fractions of agglutinated particles resulting from the separating process.

The alternating current magnetic field $H_{AC}$ may have a frequency significantly higher than the critical slipping frequency of a single magnetic particle. The frequency may be at least a factor 10, 100 or 1000 higher than the critical slipping frequency. Alternatively, the assay may be performed at or near the critical slipping frequency. It is an advantage of embodiments according to the present invention that the method may be applied in a wide range of frequencies for the applied magnetic field.

Measuring an effect may comprise measuring at least one of a magnetic signal, an optical signal or electrical signal, or a combination thereof. Measuring of an optical signal, e.g. a luminescence signal, may be detection of the optical properties of the particle using optical techniques such as scattering, evanescent-field techniques, wide-field imaging microscopy, confocal laser scanning microscopy, etc. The measuring may for example also be measuring of a magneto-optical or electro-magnetic signal.

The assay may be positioned in the proximity of a surface of the at least one sensor element.

The direction of the generated alternating current magnetic field $H_{AC}$ may be substantially parallel to the surface of the at least one sensor element. Substantially parallel thereby may be making an angle between 0° and 20° with the surface of the sensor element, e.g. between 0° and 10° with the surface of the sensor element.

The magnetic sensor may be any suitable sensor based on the detection of the magnetic properties of the particle e.g. a coil, a wire, magneto-resistive sensor, giant magneto-resistive sensor, magneto-strictive sensor, Hall sensor, planar Hall sensor, flux gate sensor, SQUID, magnetic resonance sensor, etc.

The measuring may be performed in a region being at a distance of less than 10 micrometer, preferably 5 micrometer, more preferably 1 micrometer from a surface of the sensor element. The separation process may be performed within a substantially confined volume of the assay. Beneficially, the measuring with the sensor element of the effect of $H_{AC}$ on a magnetic property of the one or more the magnetic labels may be performed in a spatial area near the sensor element. Thus, the invention may be different from on-surface measurement, but can also be applied for on-surface measurement. More specifically, the measuring may be performed within a spatial area of 10 micrometer, in particular 5 micrometer, and more particular 1 micrometer near the said sensor element. Even ranges of 200 micrometer, in particular 100 micrometer, more in particular 50 micrometer near a surface of the sensor may be applied.

The separation process may be performed by magnetic forces acting on at least a portion of the magnetic particles in the assay, said magnetic forces originating from an inhomogeneous magnetic separation field ($H_{SEP}$).

The magnetic forces ($H_{SEP}$) applied for separation may be different from the AC magnetic field. It is an advantage of embodiments according to the present invention that this facilitates a more specific separation process.

An agglutination enhancement magnetic field ($H_{ENH}$) may be applied for enhancing the agglutination process. The agglutination enhancement magnetic field ($H_{ENH}$) may be applied prior to and/or simultaneously with the magnetic separation field ($H_{SEP}$).

The effect of the alternating current magnetic field $H_{AC}$ may be measured over time. The effect of the alternating current magnetic field $H_{AC}$ on the one or more magnetic particles can be derived as an end-point measurement, as well as by recording signals in function of time, continuously or intermittently, thereby obtaining a temporal measurement. Interval of times may range from a second up to an hour, typical 1 to 10 minutes or in particular from 1 to 5 minutes. When measuring the effect of $H_{AC}$ on one or more of the magnetic particles over time, it may be for example be possible to obtain an indication of a size distribution of the agglutinated particles, or it may be possible to obtain an indication of the kinetics of the agglutination process.

The method further may comprise the step of determining a size distribution of the agglutinated particles.

The method may comprise measuring different size fractions of the agglutinated particles using a plurality of sensors resulting from said separating.

The assay may be a biochemical assay.

The present invention also relates to a kit for quantitatively measuring one or more agglutination parameters of particles in a target-induced agglutination assay according to the above described method, wherein the kit comprises at least one magnetic particle being capable of binding to the target.

The present invention also relates to a device for measuring one or more agglutination parameters in a target-induced agglutination assay, the device comprising an agglutinator means for performing an agglutination process resulting in agglutinated particles comprising at least one magnetic particle, the agglutinated particles being unattached to any surface, at least one sensor element, and a magnetic field generating means for applying an AC magnetic field to the assay. The sensor element may be arranged for measuring on the unattached agglutinated particles an effect of the AC magnetic field on the one or more magnetic particles, the measured effect being indicative of the one or more agglutination parameters. The effect of the AC magnetic field may be an effect on a magnetic property of the one or more magnetic particles. The device may have a non-functionalized surface or an assay a-specific functionalized surface.

The device further may comprise concentration and/or separation means for performing a concentration process of particles near the sensor surface or a separation process in dependency on the size of the agglutinated particles.

The device may further comprise controlling means for controlling the frequency of the generated AC magnetic field to be significantly higher than the critical slipping frequency of a single magnetic particle. The frequency may be at least a factor 10 higher than the critical slipping frequency.

The at least one sensor element may be any of an optical sensor element, a magnetic sensor element such as e.g. based on a Hall probe or magnetoresistive sensor, an acoustic sensor element, an electrical sensor element, etc.

The invention is particularly, but not exclusively, advantageous for obtaining a method for studying agglutination of particles including one or more magnetic labels or magnetic particles in a more quantitative manner than hitherto disclosed. In particular, this is obtained due to the low-noise magnetic measurement technique applied, and/or the improved separation of the agglutinated particles prior to and/or during measurement of a property of one or more magnetic particles, which provides an improved sensitivity of the desired agglutination parameters. With respect to the sensitivity in terms of the number of measurable particles, experiments performed have shown that the present invention may be at least an order of magnitude more sensitive than devices of the prior art.

As a further advantage, the method facilitates measurement of a property of agglutinated particles, that are not bound to a surface but reside in the vicinity of the sensor element, e.g. the sensor surface or any surface of the reaction chamber wherein the agglutination assay may be contained. The particles being free from binding to any surface may be particularly beneficial as complicated surface structuring (such as surface patterning and surface modification) can be superfluous, and hence this can result in significantly simplified manufacturing of sensing devices, e.g. magnetic sensing devices.

Agglutination parameters may include, but need not be limited to, the size of the agglutinates formed, the total amount of magnetic material in the form of agglutinates comprising more than 1 individual magnetic particle, the size distribution of the agglutinates, the magnetic particle number distribution of the individual particles forming the agglutinates, the ratio of non-agglutinated individual magnetic particles to agglutinated individual particles, etc.

The method of the present invention may be used with several biochemical assay types, e.g. binding/unbinding assay, sandwich assay, competition assay, displacement assay, enzymatic assay, amplification assay, etc.

The method of this invention may be suited for sensor multiplexing (i.e. the parallel use of different sensors and sensor surfaces), label multiplexing (i.e. the parallel use of different types of labels) and chamber multiplexing (i.e. the parallel use of different reaction chambers). The methods described in the present invention may be used as rapid, robust, and easy to use point-of-care biosensors for small sample volumes, but can also be used in laboratory instrumentation.

It is an advantage of embodiments according to the present invention that the reaction chamber containing the sample during the test may be a disposable item to be used with a compact reader, containing the one or more magnetic field generating means and one or more detection or measuring means. Also, the methods of the present invention may be used in automated high-throughput testing for centralized laboratories. In this case, the reaction chamber is e.g. a well plate or cuvette, fitting into an automated instrument.

It is an advantage of embodiments according to the present invention that the separation in dependency of size, if performed, does not need to be performed in another sample container or in a different process location, but can take place where the measurement is performed.

It is an advantage of embodiments according to the present invention that the applied AC magnetic field may have a frequency which is higher than the critical slipping frequency of a given type of magnetic particle under given environmental circumstances, as is further specified herein. The value of the critical slipping frequency can be obtained according to methods known to the skilled person/a method such as the one described herein.

It is an advantage of embodiments according to the present invention that the reagents for performing the agglutination assay including the magnetic labels may exist in a dry form on the device. The dry reagents can then be dissolved and dispersed by the addition of a fluid sample. This is advantageous for ease-of-use and storage of the device.

Particular and preferred aspects of the invention are set out in the accompanying independent and dependent claims. Features from the dependent claims may be combined with features of the independent claims and with features of other dependent claims as appropriate and not merely as explicitly set out in the claims.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIGS. 17a and 16b illustrates the effect of the frequency and magnitude of $H_{AC}$ on the rotation rate of a non-permanent magnetic particle as can be used in embodiments according to the present invention.

Figure 1:
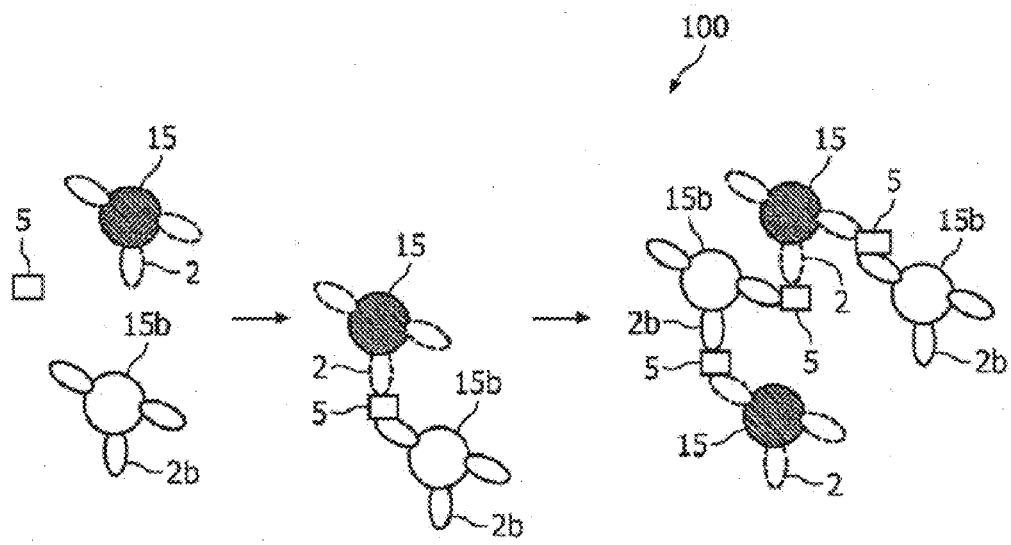
FIGS. 1, 2, and 3 are schematic reactions of an agglutination assay as can be used in embodiments according to the present invention.

In the different figures, the same reference signs refer to the same or analogous elements.

DETAILED DESCRIPTION OF THE EMBODIMENTS

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms "bottom", "above" and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may refer to the same embodiment. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The terms "generating means" and "generator" may be used interchangeably. Also the terms "controlling means"

and "controller" may be used interchangeably. Likewise, the terms "sensor" and "sensor element" may be used interchangeably.

"In function of time" or "over time" as used herein, refer to both in a continuous and discontinuous manner. In a discontinuous manner may be at predefined intervals, regularly or irregularly spaced.

The terms "agglutination" or "clustering" as used herein for the purpose of the present invention, refer to the formation of a mass, a group or a cluster by the union of at least 2 separate elements. The terms "agglutination" and "clustering", and likewise the terms "agglutinated" and "clustered", may to that respect, be used interchangeably. In particular, "agglutination" relates to the formation of such a mass or group due to a specific interaction between the elements.

For the purpose of the present invention, the term "magnetic particle" is to be interpreted broadly such as to include any type of magnetic particles, e.g. ferromagnetic, paramagnetic, superparamagnetic, etc. as well as particles in any form, e.g. magnetic spheres, magnetic rods, a string of magnetic particles, or a composite particle, e.g. a particle containing magnetic as well as optically-active material, or magnetic material inside a non-magnetic matrix. Optionally, the magnetic or magnetizable objects may be ferromagnetic particles which contain small ferromagnetic grains with a fast magnetic relaxation time and which have a low risk of aggregation of particles due to the magnetic properties of the particles alone. The present invention will be described by means of the magnetic or magnetizable objects being magnetic particles.

The term "target" as used herein for the purpose of the present invention refers to an element to be detected and/or quantified in the methods according to the present invention, i.e. the element in a sample that plays an inductive role in the agglutination process according to embodiments of the present invention. A non-limiting list of examples of target molecules envisaged by the present application is provided in the description.

The term "reaction chamber" as used herein refers to any item that may serve as a container to hold the reaction or agglutination assay. Said container is optionally detachable from the device or instrument used for performing the method of the present invention, i.e. the reaction chamber may be an integrated part of the device or instrument as well as an independent object that can be placed on, in or near the instrument and be removed again.

The term "unattached" as used herein refers to a situation where the object is free from any form of attachment, connection or interaction with a specified other object or surface, in particular where the object is free from any form of object specific attachment or specific interaction, e.g. not attached by a specific chemical or biochemical bond or interaction.

In a first aspect, the present invention provides a method for measuring agglutination involving one or more magnetic particles in a target-induced agglutination assay. Such an assay may be performed in a reaction chamber. The method comprises providing magnetic particles in an assay whereby the magnetic particles are capable of binding to a target. Such providing may comprise bringing both the assay and the magnetic particles in contact with each other. The magnetic particles may be obtained from a shelf or may be already present in the device. They may be present in any suitable form in the device. The sample may be obtained in any suitable way and introduced in the reaction chamber in any suitable way, e.g. via a syringe, by filling a cavity, etc. The method according to the embodiments of the invention can be used with several assay types, such as binding/unbinding assay, sandwich assay, competition assay, displacement assay, enzymatic assay, etc. The process may involve a variety of elements comprising different classes of molecules and biological entities, e.g. DNA, RNA, proteins, small molecules. In addition to molecular assays, also larger moieties can be detected or probed, e.g. cells, viruses, or fractions of cells or viruses, tissue or tissue extract, etc. Molecular targets often determine the concentration and/or presence of larger moieties, e.g. cells, viruses, or fractions of cells or viruses or bacteria, tissue extract, etc. The magnetic particles can have small dimensions, e.g. be nanoparticles. With nanoparticles are meant particles having at least one dimension ranging between 0.1 nm and 10000 nm, preferably between 3 nm and 3000 nm, more preferred between 10 nm and 1000 nm. The magnetic particles can acquire a magnetic moment due to an applied magnetic field (e.g. they can be paramagnetic) or they can have a permanent magnetic moment. The magnetic particles can be a composite, e.g. consist of one or more small magnetic particles inside or attached to a non-magnetic material. As long as the particles generate a non-zero response to the frequency of an AC magnetic field, i.e. when they generate a magnetic susceptibility or permeability, they can be used. Magnetic particles with different shapes can be used, e.g. spherical, rod-like, two-bead clusters. The magnetic particles may display further properties, e.g. optical properties such as fluorescence. These differing properties of the magnetic particles may be used for multiplexing in the assay. Label-multiplexing may occur by using distinguishable properties for different particles within the same sensor category e.g. different magnetic materials yielding distinguishable signals for magnetic sensor elements, or by using properties selected from different sensor categories e.g. using a combination of magnetic and optical labels which will each be selectively measured by respectively a magnetic sensor element and optical sensor element.

The method furthermore comprises performing an agglutination process for the assay with magnetic particles resulting in agglutinated particles. The agglutinated particles comprise at least one magnetic particle. Cluster formation or agglutination may be a measure for the presence of the target in the sample, whereby the target induces agglutination. In embodiments of the present invention agglutination of magnetic particles and assay particles is performed. For easy correlation of the sensor signal and target presence, two-particle clustering may be favored above multiple-particle clusters. To favor two-particle clusters above multiple-particle clusters, for example a concentration of particles or a concentration of capture molecules on the particles may be used that highly exceeds the eventual target concentration. Also, biochemistries can be used that in principle do not allow the formation of clusters of more than two units. For example, a sandwich-type assay format is used, with on one side a magnetic particle with specific antibodies, and on the other side a fluorescent label with only one antibody per label.

According to embodiments of the present invention, the agglutination occurs in the bulk solution and does not require binding to a surface. This can be advantageous for assay simplicity, assay speed, fabrication simplicity, and low costs.

Particularly in rapid assays and in assays with low target concentrations, very low numbers of events need to be detected. According to embodiments of the present invention, it becomes possible to rapidly and accurately measure low numbers of clusters in a background of many un-clustered species, and/or to detect a low number of un-clustered species in a background of a high number of clusters.

The method may optionally comprise, after performing said agglutination process and prior to the measuring, applying a concentration and/or separation process.

The separation process can be in dependency on the size of the agglutinated particles. The application of the separation process may be performed by applying a magnetic field for separating the particles, e.g. an inhomogeneous magnetic field. Further examples of the separation process will be described in more detail below. Alternatively, the separation process may not be performed.

The concentration process in particular may have the effect of concentrating the particles to be measured near a sensor surface. This particular embodiment may have the advantage to improve the sensitivity of the method for detection of said particles.

Figure 18:
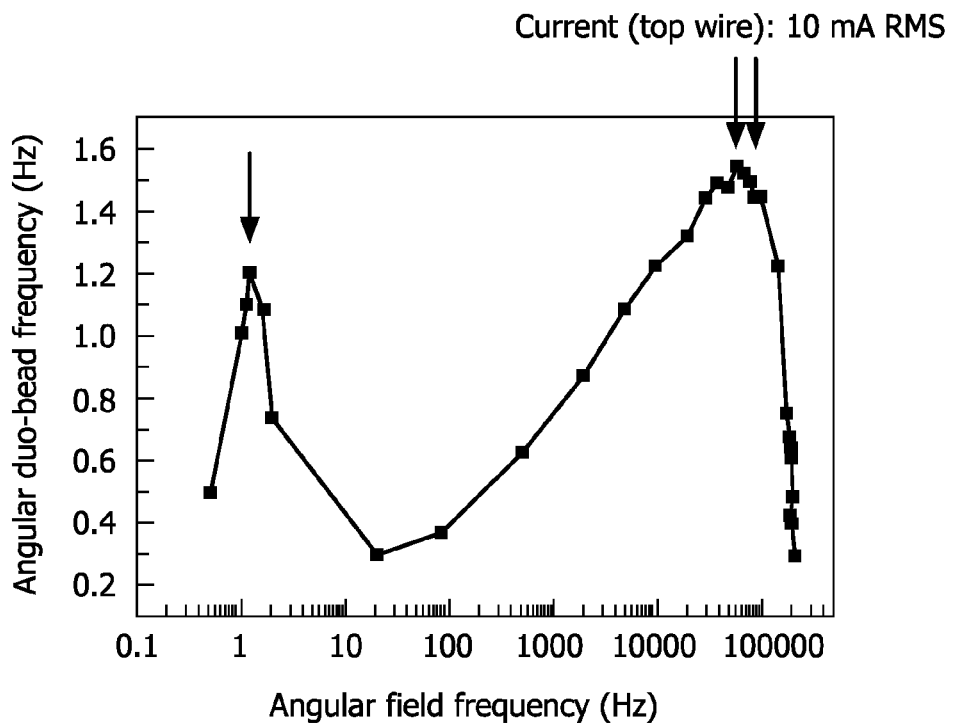
FIG. 18 illustrates the effect of the frequency of $H_{AC}$ on the rotation rate of a two-bead cluster of magnetic particles as can be used in embodiments according to the present invention.

The method also comprises applying an alternating current (AC) magnetic field ($H_{AC}$) to the assay. The assay thereby may be in the vicinity of at least one sensor element used for measuring an effect. Such an alternating current magnetic field may be generated in any suitable way such as using wires, coils, magnetic materials, electromagnets or the like. It may be generated on-chip or off-chip. On-chip means that the generator is integrated in the device, whereas off-chip refers to the generator being external to or independent from the device. In embodiments according to the present aspect of the invention, the method for measuring target-induced agglutination makes use of the finding that magnetic particles can rotate in an AC magnetic field. The magnetic particles rotate in such a rotating magnetic field for frequencies of the applied field up to a maximum at a certain frequency, the so-called critical slipping frequency. Above the critical slipping frequency the physical rotation of the magnetic particle cannot follow the rotations of the applied magnetic field. As will be illustrated further, it has been surprisingly found that for frequencies substantially higher than the critical slipping frequency, the physical rotation of the magnetic particle increases again. In other words, it has surprisingly been found that frequencies substantially higher than the critical slipping frequency also can be used for determining agglutination parameters. The frequency of the applied AC magnetic field $H_{AC}$ may for example be a factor 10 higher than the critical slipping frequency. The $H_{AC}$ frequency may be at least 10 times higher than the critical slipping frequency, or at least 100 times higher, or at least 1000 times higher. The critical slipping frequency is typically a few Hz whereas the rotation caused by neel relaxation, i.e. rotation at substantially higher frequency of the rotating magnetic field, starts to dominate above a few kHz increasing up to a few MHz. For the purpose of this embodiment, the applied $H_{AC}$ frequency is between about 10 HZ and about 10 MHz, more in particular between about 100 Hz and about 1 MHz. The actual frequency desired depends on the size/type of magnetic particles used. To obtain maximum signal it is advantageous to use a frequency that is close to the second maximum (as illustrated in FIG. 18) regarding the measured effect of the applied AC field. For the beads used in the experiments illustrated by FIG. 18, the desired frequency is around 600 kHz. Depending on the assay and the type of particles used, this might be considerably lower/higher due to the strong dependence of Neel relaxation time on e.g. grain size of the magnetic particles used. The critical slipping rate can be measured optically or magnetically, by studying particle rotation as a function of the applied field rotation frequency. Within the framework of the present invention, there are two possibilities for determining the critical slipping frequency. A first option is characterizing a batch of beads prior to the agglutination assay so the critical slipping frequency is known before beads are used in the actual device in which the assay is performed, or before the beads are used in a method according to the invention. Alternatively, the critical slipping frequency is determined in the device in which also the agglutination assay is performed. The critical slipping frequency can be determined by optical microscopy on a rotating bead while sweeping the field frequency from 0 Hz up to a frequency well above the critical slipping frequency. The critical slipping frequency can also be determined by using a magnetic field sensor that measures the dipole field of the rotating bead while sweeping the frequency of the applied field. Lock-in detection of the output signal gives the sensor output at the applied field frequency. Once the permanent magnetic moment of the bead can not follow the applied field (critical slipping frequency) the signal at the actuation frequency shows a drop.

The frequency at which the applied AC magnetic field $H_{AC}$ is operated thus may be higher than the critical slipping frequency. Working at higher frequencies may be advantageous over working at the critical slipping frequency. Several advantages may result from operating the $H_{AC}$ at much higher frequencies than the critical slipping frequency. High-frequency excitation minimizes the dipole-dipole interactions between magnetic particles, which improves the sensor reproducibility. The signal-to-noise ratio and the detection sensitivity are high due to the use of a modulation technique. The generated AC magnetic field applied to the assay, e.g. in the vicinity of the sensor 11, enables measurement of the effect induced to a magnetic property of the one or more magnetic particles 15. Such a magnetic property may be a property influenced by an AC magnetic field.

The method also comprises measuring with the at least one sensor element, an effect of the $H_{AC}$ on the one or more magnetic particles unattached to any surface of the reaction chamber, wherein the measured effect is indicative of one or more agglutination parameters. The alternating current magnetic field may act on a magnetic property of the one or more magnetic particles. The measurement of the $H_{AC}$ effect indicative for agglutination provides information with respect to the presence of the target in a sample. Such information may be both qualitative and quantitative. Qualitative measurement of agglutination indicates the nature or identity of one or more targets present in a sample. Quantitative measurement of agglutination indicates in which amount one or more targets are present in the sample. Measurement of the $H_{AC}$ effect may be optically measuring, acoustically measuring, magnetically measuring, electrically measuring, etc of such an effect, depending on the physical nature of the effect. For example, optically measuring may be based on detection of evanescent radiation, detection of fluorescent radiation, detection of phosphorescence, detection of scattered light, etc. The measured effect can be correlated to the number of magnetic particles, and if a separation process is performed, the number of particles can be transformed into a size distribution.

Figure 14:
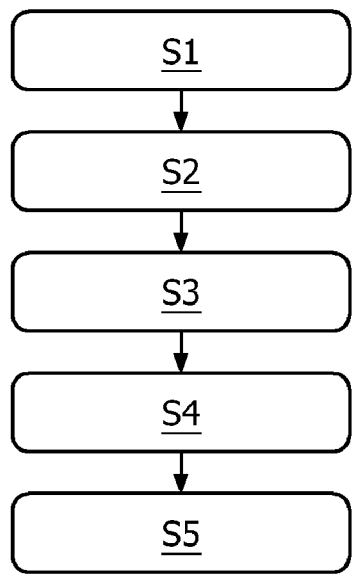
FIG. 14 is a flow-chart of a method according to an embodiment of the present invention.

By way of illustration, the present invention not being limited thereto, a flow-chart of a method according to the invention for measuring one or more agglutination parameters of particles in a target-induced agglutination assay is shown in FIG. 14, illustrating standard and optional steps of the method. The method thereby comprises steps S1, S2, S4 and S5, and optionally comprises step S3. Step S1 corresponds with providing magnetic labels 3, 15 in the assay, said magnetic labels being capable of binding to the target 5. Step S2 corresponds with performing an agglutination process resulting in agglutinated particles 100 comprising one or more magnetic particles. Optional step S3 corresponds to performing a concentration and/or separation process. The separation process can be in dependency on the size of the agglutinated particles e.g. by applying a separation force $F_{SEP}$. Step S4 comprises applying an alternating current magnetic field $H_{AC}$ to the assay, wherein the assay, and thus the reaction chamber wherein the assay is kept during the measurement, is in the vicinity of at least one sensor element 11, such that an induced effect will be measurable by the at least one sensor element 11. Step S5 comprises measuring with the sensor element an effect of the $H_{AC}$ on the one or more magnetic labels or particles 3,15 free from binding to any surface of the reaction chamber, wherein the measured $H_{AC}$ effect is indicative of the one or more agglutination parameters.

By way of illustration, the present invention not being limited thereto, a number of examples are described in more detail as well as a number of standard or optional steps of the method, the present invention not being limited thereto.

In a first example, a number of schematic reactions of agglutinations assays are shown, which can be used in embodiments of the present invention. FIG. 1 depicts an agglutination assay in which magnetic particle or label 15 becomes attached to magnetic particle 15*b* through a sandwich structure consisting of target 5 bound by binding moieties 2, and 2*b* attached to particle 15 and 15*b*, respectively. This format can be used when the target has at least two binding sites, typically such as protein or peptide antigens with multiple paratopes, nucleic acids (DNA, RNA), and antibodies with multiple epitopes, etc., but potentially the target may be relatively small such as haptens, small molecule drugs, hormones, metabolites, etc. Magnetic particle 15 becomes attached to magnetic particle 15*b* through a sandwich structure consisting of target 5 bound by moieties 2, and 2*b* attached to particle 15 and 15*b*, respectively, resulting in formation of agglutinated particles 100. The two binding sites can be distinct, in which case binding moieties 2 and 2*b* are different. Alternatively, the two binding sites can be identical, in which case 2 and 2*b* are the same. Binding moieties 2 and 2*b* can be directly attached to the magnetic particles or through some intermediate binding groups, such as for example protein G, streptavidin, biotin, protein A, IgG antibodies etc, the invention not being limited thereto. One or both of the binding moieties 2 and 2*b* can be present already attached to the particle or independent of the particles in which case both the binding moieties and particles must have on them intermediate binding moieties that allow the particles to attach to the binding moieties 2 and 2*b*. Thus, the binding of the magnetic particle 15 and the target 5 can be indirect in the context of the present invention. For targets 5 which are small and only have one binding site (such as small molecules, hapten, drugs, hormones, and metabolites) an inhibition or competitive format can alternatively be employed.

Figure 2:
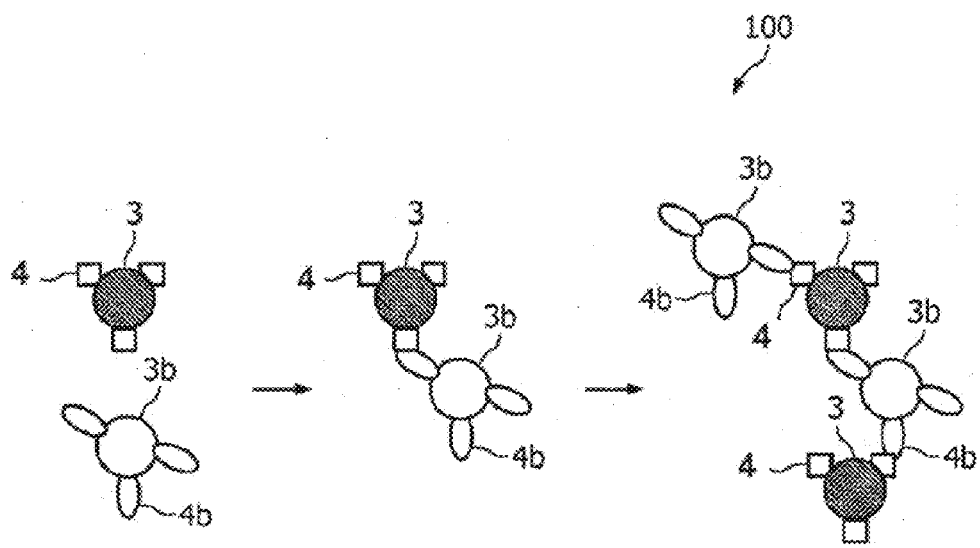

FIG. 2 depicts such an assay in which magnetic particle 3 aggregates with particle 3*b* through moiety 4, attached to 3, which can be bound by binding-moiety 4*b* attached to particle 3*b*. Moiety 4 can be a target homologue and when the target is added, it binds to moiety 4*b* and inhibits the aggregation of the particles. It is advantageous that the target is added before aggregation has begun, because the aggregation may be irreversible or the aggregates difficult to disperse. This can be achieved by spatially separating moiety 4 and 4*b* and letting the target first react with 4*b*. Similar to the sandwich format, binding moiety 4*b* can be independent of the particle and be attached during the reaction by intermediate binding moieties. The binding moieties are specifically designed to recognize the target and can be molecules such as antibodies, nucleic acids, aptamers, peptides, proteins, and lectins. The components can bind in any order, although it is preferable to have the binding moieties already attached to the particles before exposure to the target for actuation purposes. Particles can be up to 2 micrometer, with a preference for particles less than 1 micrometer due to their larger surface-to-volume ratio which will result in a higher dynamic range. The agglutination arises from the binding of multiple particles to one another, and results in agglutinated particles 100.

Figure 3:
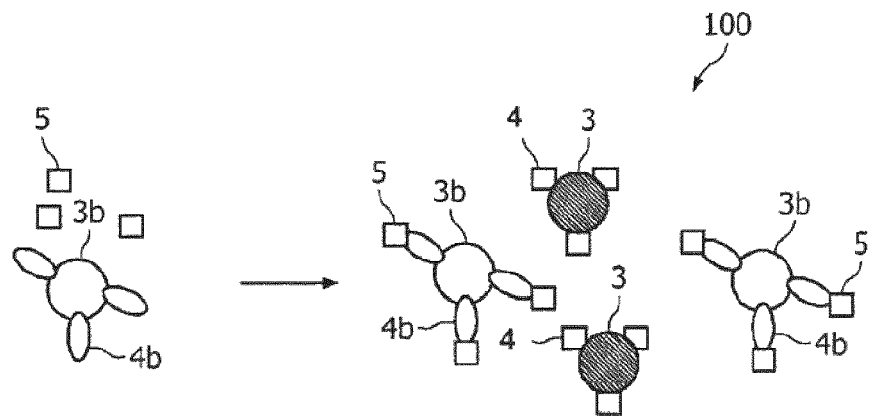

FIG. 3 depicts an assay, where moiety 4 can be a target homologue, and when the target 5 is added, it binds to moiety 4*b* and inhibits the aggregation of the particles. Thus, it is to be understood that within the context of the present invention, an agglutination process advantageously includes a process where inhibition of agglutination is studied.

In a second particular set of examples, measurement of effects with different detection techniques is illustrated, the present invention not being limited thereto. In one example, radiative labels, such as e.g. luminescent or fluorescent labels, are embedded in or attached to the magnetic particles that are used. For example, antigens may be coupled to fluorescent magnetic particles or to both fluorescent and non-fluorescent magnetic particles. Excitation of the fluorescent magnetic particles can be done using an irradiation source, such as for example via focused laser beam or via evanescent field excitation allowing optical detection of such labels. Detection can be done in any suitable way, such as for example using confocal detection or using a high-NA lens. The use of fluorescent magnetic particles enables multiplexing by using different fluorophores, which differ in excitation and/or emission wavelengths. As another example of an embodiment, detection can be done optically, using fluorescent labels (initially either free, or embedded in or attached to a non-magnetic particle) in combination with magnetic particle labels. The measurement of agglutination in this example then may not be based on cluster formation of magnetic particles but on the increase in fluorescence of magnetic particles. For example, antigens, labelled with either a fluorescent or magnetic particle label, are mixed, and exposure to a sample containing antigen-specific antibodies will lead to binding of fluorescent labels to magnetic particle labels. For this embodiment, magnetic particles can be actuated to a non-binding sensor surface and surface specific detection of fluorescence labels can be done. Surface specific excitation of the fluorophores can be done using a radiation source, e.g. using a focused laser beam or via evanescent field. Detection can be done either via confocal detection (surface sensitive detection) or using a high-NA light-collection lens (not surface sensitive). By using this method the background fluorescence from excess labels and from the sample fluid itself can be reduced or even minimized. Multiplexing of the assay based on differential labeling of the particles can be easily envisioned making use of different fluorescent labels. Optical detection can be done also by Surface-Enhanced Resonance Raman spectroscopy (SERRS). SERRS is an ultra-sensitive method for detection of molecules or species by adsorption of the molecule or species that is optically labeled on colloidal particles, e.g. silver particles. The optical label is a suitable dye molecule (such as Rhodamine) causing plasmon and dye resonance when the colloidal particles cluster in a controlled way. It is known that magnetic particles exist with a metallic coating. If for example antigens (to which the target, i.e. antibodies, binds) are coupled to such silver-coated magnetic particle, while the antigens are also coupled to a suitable dye, antigen-specific antibodies will lead to linking of the dye to the silver-coated magnetic particles. Magnetic actuation will lead to cluster/pillar formation which will lead to dye resonance. SERRS can be detected after actuation to a non-binding sensor surface in an evanescent field. In such a set-up, antibody detection can be done in a single chamber omitting fluid wash steps since the detection is surface specific and not disturbed by unbound dyes from solution.

In another example, a magnetic sensor may be used, such as for example a Hall sensor, a magnetoresistive sensor such as for example an GMR, TMR or AMR sensor. In a particular example, the magnetic sensing may take advantage of the fact that a particular frequency may be used for the applied AC magnetic field. In the low frequency regime, i.e. at frequencies e.g. below 100 Hz, the 1/f noise of the magnetic sensor element dominates. 1/f noise is caused by point-to-point fluctuations of the current and is proportional to the inverse of the frequency. In magnetoresistive sensors, 1/f noise originates from magnetic fluctuations in the free layer. When the frequency of the generated AC magnetic field is 100 Hz or above, the dominating 1/f noise is significantly reduced compared to the prior art, resulting in an improved signal to noise ratio (SNR). It is advantageous when the frequency of the AC magnetic field is further increased to a value where the thermal white (Nyquist) noise level becomes dominant over the 1/f noise level. As mentioned in WO 2005/010542, above a certain corner frequency $f_c \approx 50$ kHz the thermal white noise of GMR sensors becomes dominant. The white-noise level limits the theoretically achievable detection limit.

Figure 4:
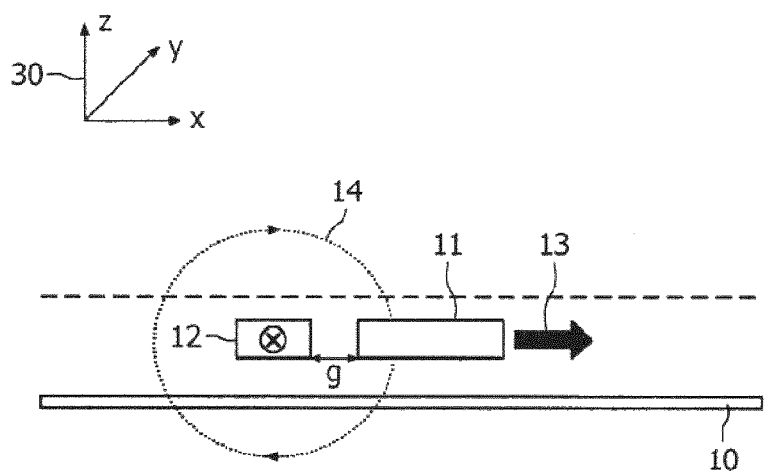
FIG. 4 is a cross-sectional view of a sensor device using a magnetic sensor whereby no magnetic particles are present, being an illustration of an embodiment according to the present invention.
Figure 5:
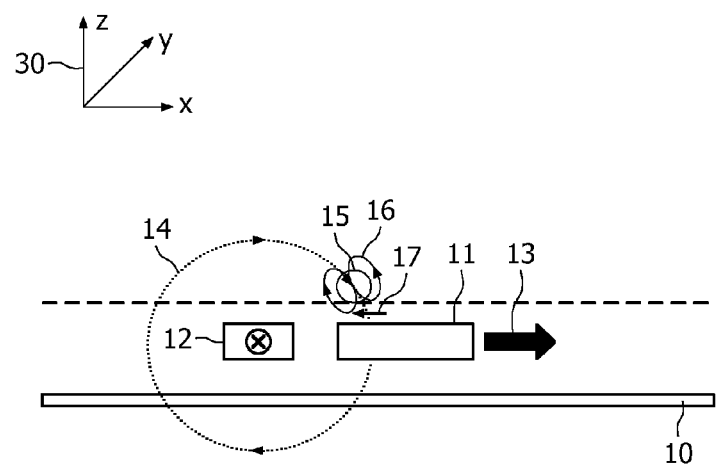
FIG. 5 is a cross-sectional view of a sensor device using a magnetic sensor whereby magnetic particles are present, being an illustration of an embodiment according to the present invention

FIGS. 4 and 5 are cross-sectional views of an exemplary sensor device according to an embodiment according to the present invention wherein a magnetic sensor is used, respectively without and with magnetic particles 15. For illustrative purposes the invention will be explained below with respect to a biosensor. The biosensor detects magnetic particles in a sample such as a fluid, a liquid, a gas, a visco-elastic medium, a gel or a tissue sample. The device may comprise a substrate 10 and a circuit e.g. an integrated circuit. A measurement surface of the device is represented by the dotted line in FIG. 4 and FIG. 5. The substrate may comprise semiconductor material, glass, plastic, ceramic, silicon-on-glass, silicon-on sapphire substrates. The circuit may comprise a magnetoresistive sensor 11 as a sensor element and a magnetic field generator in the form of a conductor 12. The magnetoresistive sensor 11 may for example be a GMR, a AMR or a TMR type sensor. The magnetoresistive sensor 11 may for example have an elongated, e.g. a long and narrow stripe geometry but is not limited to this geometry. Sensor 11 and conductor 12 may be positioned adjacent to each other (FIG. 4) within a close distance g. The distance g between sensor 11 and conductor 12 may for example be between 1 nm and 1 mm; e.g. 3 µm. In FIGS. 4 and 5, a co-ordinate system is introduced to indicate that if the magnetic sensor device is positioned in the xy plane, the magnetic sensor 11 mainly detects the x-component of a magnetic field, i.e. the x-direction is the sensitive direction of the magnetic sensor 11. The arrow 13 in FIG. 4 and FIG. 5 indicates the sensitive x-direction of the magnetoresistive sensor 11 according to the present invention. Because the magnetic sensor 11 is hardly sensitive in a direction perpendicular to the plane of the sensor device, in the drawing the vertical direction or z-direction, a magnetic field 14, caused by a current flowing through the conductor 12, is not detected by the sensor 11 in absence of magnetic nano-particles 15. By applying a current to the conductor 12 in the absence of magnetic nano-particles 15, the sensor 11 signal may be calibrated. This calibration is preferably performed prior to any measurement. When a magnetic material (this can e.g. be a magnetic ion, molecule, nano-particle 15, a solid material or a fluid with magnetic components) is in the neighbourhood of the conductor 12, it develops a magnetic moment m indicated by the field lines 16 in FIG. 5. The magnetic moment m then generates dipolar stray fields, which have in-plane magnetic field components 17 at the location of the sensor 11. Thus, the nano-particle 15 deflects the magnetic field 14 into the sensitive x-direction of the sensor 11 indicated by arrow 13 (FIG. 5). The x-component of the magnetic field $H_x$ which is in the sensitive x-direction of the sensor 11, is sensed by the sensor 11 and depends on the number $N_{np}$ of magnetic nano-particles 15 and the conductor current $I_c$.

Figure 6:
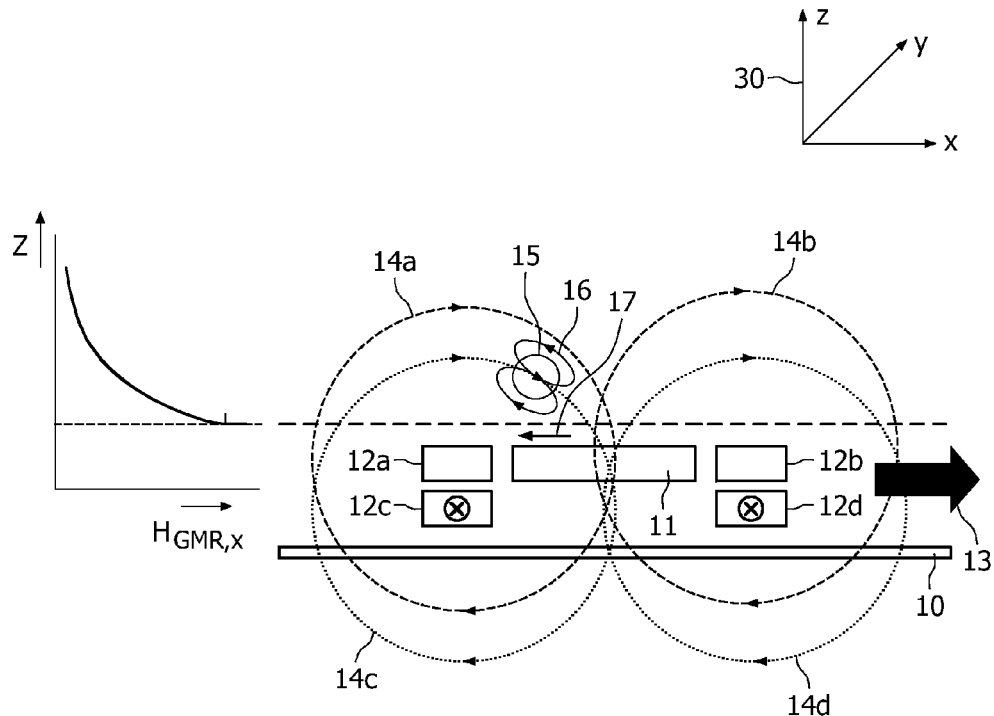
FIGS. 6, 7, and 8 are cross-sectional views of three embodiments of a sensor device of the present invention using a magnetic sensor with improved resolution in a direction substantially perpendicular to the magnetic sensor plane.
Figure 7:
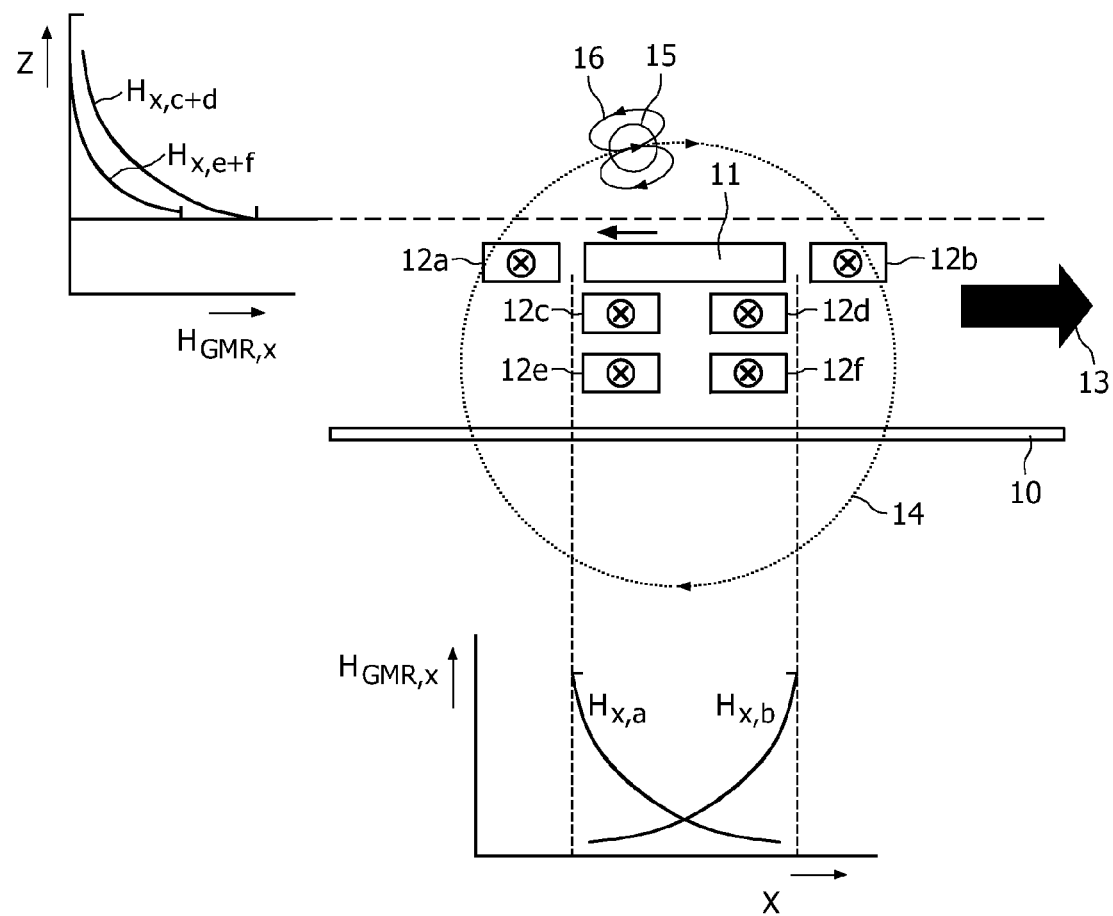
Figure 8:
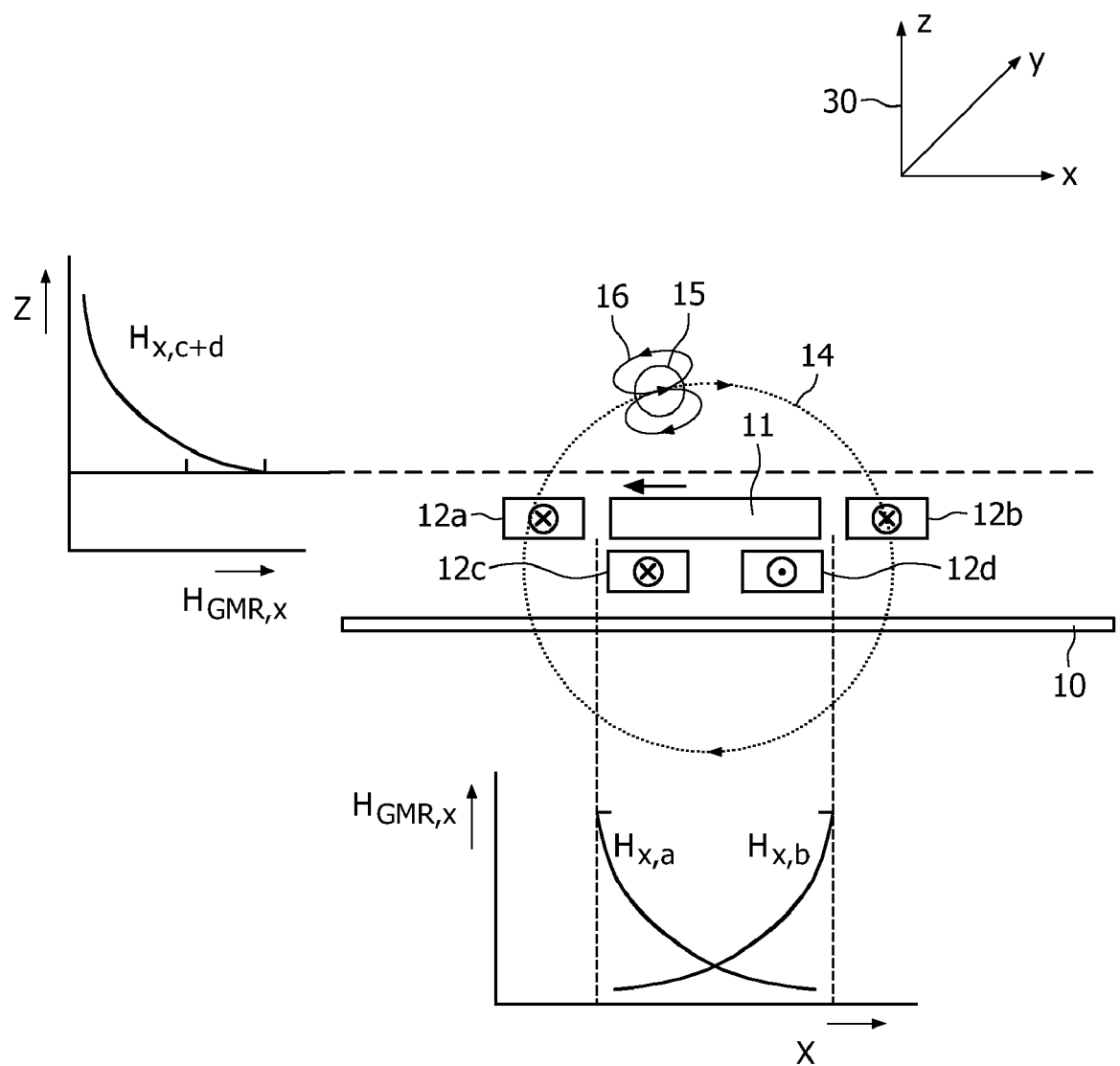

In a third particular example, sensor units and corresponding sensing methods according to embodiments of the present invention are described, which have a good resolution in the direction perpendicular to the sensor plane. FIGS. 6, 7, and 8 are cross-sectional views of three embodiments of such sensing units with improved resolution in the direction perpendicular to the sensor plane. In order to distinguish between surface- and bulk concentrations of magnetic particles 15, resolution in a direction perpendicular to the plane of the sensor element 11, which corresponds to the z-direction with the co-ordinate system introduced in FIG. 4, is required. As shown in FIG. 6 conductors 12c and 12d generate a magnetic field 14c and 14d respectively in comparison with the magnetic field 14a and 14b of conductors 12a and 12b. By combining the sensor signals originating from the four conductors 12a, 12b, 12c, 12d, information may be obtained about the concentration of the magnetic particles 15 in x and z direction. The z-resolution can be further enhanced by applying more conductors in the direction perpendicular to the plane of the magnetic sensor element 11, which as represented is the vertical or z direction. This is shown in the embodiment of FIG. 7. Conductors 12a and 12b are positioned at both sides next to the magnetic sensor 11, at the same level in a direction perpendicular to the plane of the sensor element 11. Conductors 12c, 12d, 12e and 12f are positioned between the substrate 10 and the sensor 11, the conductors 12c and 12d are at a different z-position with respect to conductors 12e and 12f. Again, combination of the sensor signals resulting from the different conductors 12a to 12f may give information about the bulk, near-surface and surface concentration of the magnetic particles 15. In still another further embodiment, the currents in conductors 12c and 12d, which are positioned at a level in between the substrate 10 and the magnetic sensor 11, have opposite directions, as illustrated in FIG. 8. In that way, conductors 12c and 12d may generate a strong field gradient in the x direction. This embodiment may be advantageous for enhancing spatial resolution.

Figure 9:
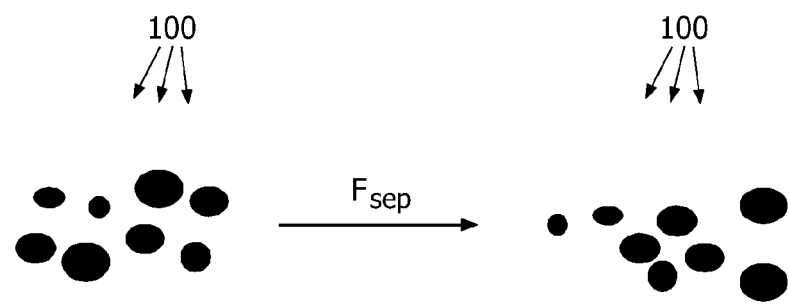
FIG. 9 is a schematic illustration of a separation process according to an embodiment of the present invention.

In a fourth particular example, the optional step of performing a separation process in dependency on the size of the agglutinated magnetic particles is described in more detail. FIG. 9 is a schematic illustration of the separation process as can be used in embodiments according to the invention for quantitatively measuring one or more agglutination parameters of magnetic labels 15 in a target-induced agglutination assay. Such a step may be performed after providing the labels and after performing the agglutination process resulting in agglutinated particles 100. In one example of the separation process, a separation force $F_{SEP}$ may be applied in one or more spatial directions, the separation force being dependent on the size of the agglutinated particles 100. The separation force $F_{SEP}$ advantageously may be an inhomogeneous magnetic field applied on the agglutinated particles 100, but other kinds of separation are also possible such as for example rotation causing a centrifugal force to separate the forces by mass, application of a hydro-dynamic pressure, application of an electrostatic separation (requires a charge on the agglutinated particles 100), etc. In addition or alternatively to the use of various forces applied for separation, size exclusion filters can also be used. It may be assumed for most agglutination assays that the number of magnetic particles 15 incorporated into the agglutinated particles 100 is directly dependent, e.g. proportionally, on the size of the agglutinated particles 100, though it may be not always be the case. If an inhomogeneous magnetic field is applied for separation, the magnetic field may be generated by the same means generating the AC magnetic field, or alternatively by dedicated magnetic generating means, e.g. arranged close the magnetic sensor element 11 for that purpose.

Figure 10:
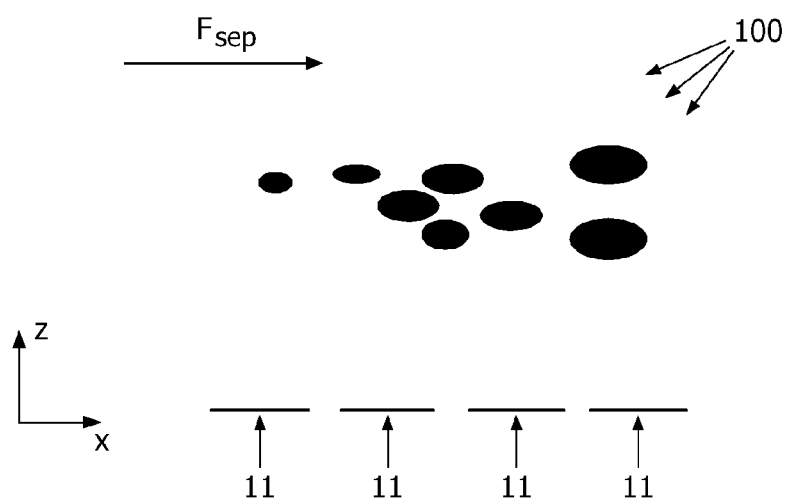
FIG. 10 is a first particular embodiment of the separation process according to an embodiment of the present invention.

FIG. 10 is one embodiment of the separation process according to the present invention, where a plurality of sensor elements 11 are arranged relative to the separated agglutinated particles 100 to facilitate a measurement of the size distribution of the agglutinated particles as illustrated in FIG. 10. The separation results in a spatial separation with respect to the different sensor elements 11 in one spatial direction, but similarly the separation can be performed also in two or three spatial dimensions.

Figure 15:
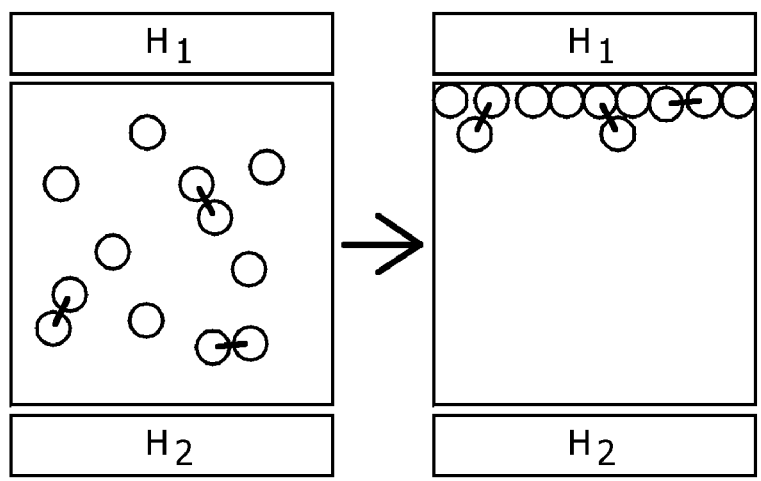
FIG. 15 is also an example of the separation process according to an embodiment of the present invention, wherein $H_1$ and $H_2$ indicate two magnetic field generating means arranged at opposite sides of the agglutination assay.
Figure 15:
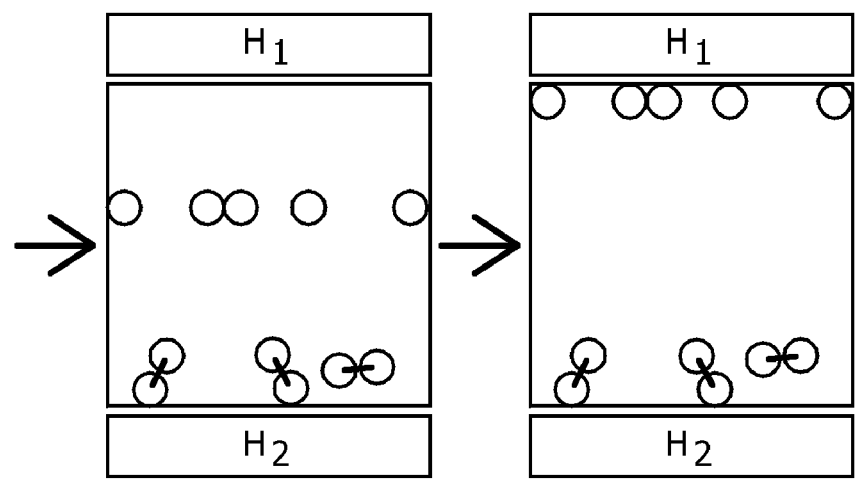

FIG. 15 also illustrates an embodiment of the separation process as can be used in embodiments according to the method of the present invention. Magnetic particles of different sizes, e.g. single versus clustered particles, or small versus large sized clusters, can be separated using magnetophoretic separation, based on the fact that their velocity in a magnetic field is directly proportional to its susceptibility to magnetic forces. Clusters of magnetic particles e.g. resulting from agglutination, will have an increased susceptibility as compared to single magnetic particles and therefore magnetophoresis can be used to separate clustered magnetic particles from single magnetic particles. Upon actuation or sedimentation to a non-binding surface, e.g. sensor surface or a surface of the reaction chamber, the change in sensor signal can be monitored in time. Since clusters will sediment faster or move faster in a magnetic field, they will arrive at the surface earlier in time. Monitoring magnetic particles near or on the non-binding surface in time will therefore be an indication for cluster formation where the measurement of agglutination parameters involves a separation step. For reproducible separation of single from clustered beads, the principle of magnetophoretic particle separation can be used, e.g. in a cartridge set-up as developed now for GMR and FTIR detection. FIG. 15 thereby shows a schematic illustration of the embodiment, indicating a reaction chamber with both underneath the sensor surface and on the opposite site above the roof of the reaction chamber an electromagnetic coil, a top and bottom coil, indicated as $H_1$ and $H_2$ respectively. Separation can be reached by first collecting the beads at the roof of the reaction chamber by turning on the top coil. If then the bottom coil is turned on, while the top coil is turned off, the magnetic particles will move towards the sensor surface. At a defined time, when the two-bead clusters are over and the single cluster are less then half way the roof-sensor distance, the top coil is turned on again. Two-bead clusters will move further down to the sensor surface, while the single beads will move back to the roof. This method will allow for end point measurement of magnetic particle clusters and does not require kinetic detection. In analogy, single magnetic particles can be magnetically separated from clustered magnetic particles in a way that the single beads reach the non-binding sensor surface, while the clustered beads are collected on a spot different from the sensor surface. One way to reach this may be by making use of the same magnetophoretic particle separation as described above, but then the other way around: beads are first collected on the sensor side, then the bottom coil is turned off and the top coil is turned on. After a defined time, when the two-bead clusters are over and the single cluster are less then half way the roof-sensor distance, the bottom coil is turned on again. Two-bead clusters will move further up to the roof, will the single beads will move back to the sensor. This example is a "1-x assay", since the presence of the target will lead to clusters, which will lead to a decreased amount of single magnetic particles detected on the sensor side. Because of the low sensitivity that is inherent to such an assay, this format is probably not preferred. The advantage of this embodiment will be that multiple cluster formation does not disturb the quantification, since not the agglutinated particles, but the decreased single magnetic particles are detected. For both options within this example, magnetophoretic separation of magnetic particles of different size can also be reached by using integrated wires. Particle separation then takes place in plane of the sensor surface. Clusters or single beads, depending on the type of experiment chosen, can be collected on the spot of the detection (above the detection wire in case of GMR or above the laser spot in case of FTIR) while single or clustered magnetic particles respectively, are collected on a spot in plane of the sensor surface, at a sufficient difference from the detection side.

Figure 11:
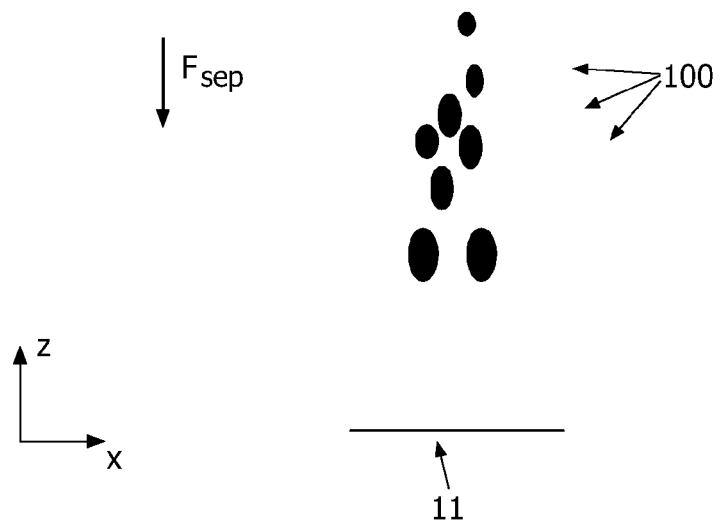
FIG. 11 is a second particular embodiment of the separation process according to an embodiment of the present invention.
Figure 12:
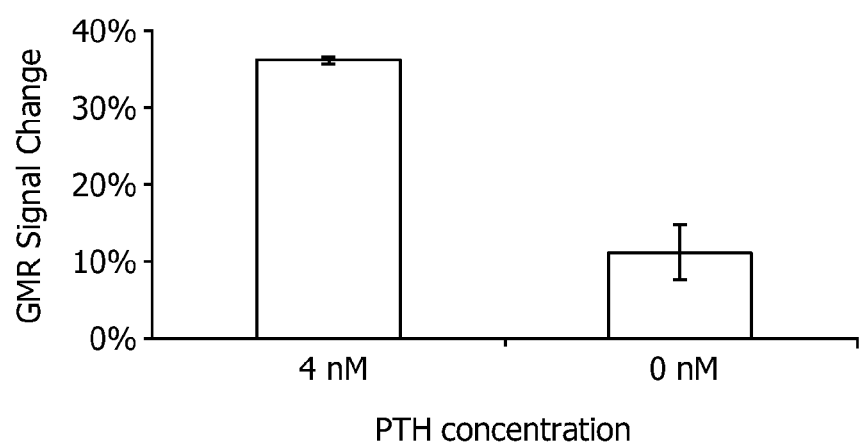
FIG. 12 is a measured GMR signal in a kinetic study of agglutination as can be used in embodiments according to the present invention.

FIG. 11 is another embodiment of the separation process according to the present invention, where a single sensor 11 is arranged relatively to the separation force $F_{SEP}$ applied so that a measurement as function of time will reveal, or at least indicate, the size distribution of the agglutinated particles 100. The separation can be characterized as a temporal separation. Time dependent measurement by the sensor 11 can also be applied for measurement of agglutination kinetics. FIG. 12 is an example of a kinetic study with a parathyroid hormone assay in which 4 nM of the analyte is first added to particles containing antibodies to PTH. The measurement is performed in a setup similar to FIG. 11 for 60 minutes. The particles aggregate in the presence of the target (200 nm) and sediment faster under weak magnetic actuation than the sample containing no analyte, the result being a significantly larger GMR signal. The separation force $F_{SEP}$ is made by an alternating current (AC) magnetic field.

Figure 13:
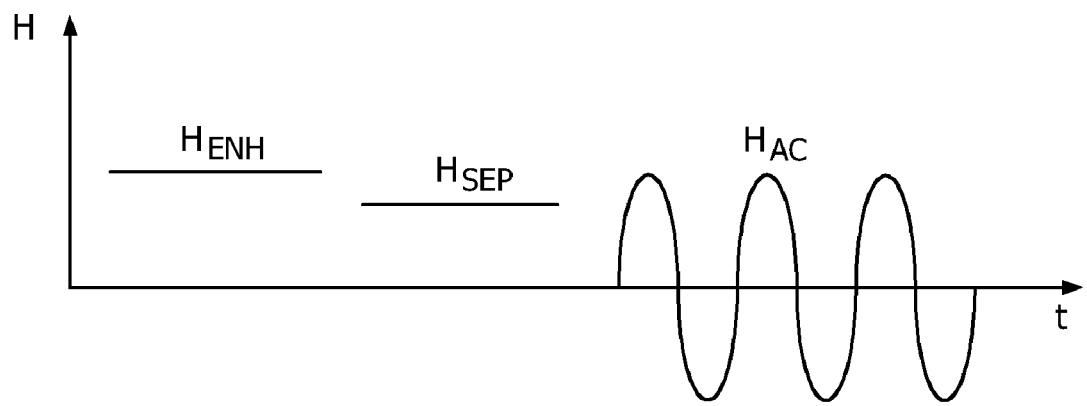
FIG. 13 is a schematic illustration of the various magnetic fields applied in an embodiment of the invention in dependency of time as can be used in embodiments according to the present invention.

In a fifth particular example, an illustration is provided on how the agglutination process optionally can be improved. The method thereby comprises applying an agglutination enhancement magnetic field ($H_{ENH}$). The agglutination enhancement magnetic field may be applied prior to or simultaneously with the magnetic separation field. By applying an inhomogeneous magnetic field ($H_{ENH}$) across the assay, the magnetic particles are actuated, and hence agglutination is increased by reversible non-specific interaction. The particles containing the binding moieties can be moved through the solution with magnetic actuation so that the number of target encounters with the binding moieties is increased. This can be used in order to enhance the speed of the assay or enhance its sensitivity. Although this can be done during agglutination, actuation is preferably performed before agglutination to have as much of the binding moieties exposed as possible. This can be achieved by exposing the target 5 first to the particle 15-binding moiety 2 complex, actuating and then exposing the target to the particle 15b-binding moiety 2b complex or vice versa, cf. FIG. 1. A similar scheme is possible for the inhibition format. In an alternative embodiment, enhancing the formation of agglutinates is performed by enhancing the magnetic particle 15 encounter with the other magnetic particles 15b after the target 5 has been attached to the binding moiety 2 and 2b, cf. FIG. 1. The magnetic forces involved do not have to be the same for this and the previous embodiment of enhancement but the magnetic field can be same for some embodiments. Although both types of enhancement can be formed simultaneously, it is preferable to perform the first form of enhancement, then add particle 15b and then perform the second form of enhancement. Magnetization of the particles is necessary for actuation. This may result in reversible aggregation of the particles under the external field. It is highly preferable to perform the assay under buffer conditions that prevent the clusters from permanently binding to one another non-specifically. The buffer can contain at least 1% proteins that prevent non-specific binding (albumins, globulins, gelatin, casein, etc.) and/or at least 0.05% detergents (Triton X-100, Tween 20 or 80 etc) and/or polymers (PVB, PEG etc.). Separation may then be performed by applying the magnetic field $H_{SEP}$ on the assay as described above. Both the separation magnetic field $H_{SEP}$ and the enhancement magnetic field $H_{ENH}$ are subject to the conditions that the fields should not be too strong or have too strong spatial gradients to prevent irreversible non-specific agglutination that will distort the measurement. With 300 nm magnite particles, the inventors have found that upper limits of the field strength of $1\times 10^4$ A/m, $1\times 10^5$ A/m, or $1\times 10^6$ A/m are suitable, whereas upper limits for the gradient may be $1\times 10^7$ A/m$^2$, $1\times 10^8$ A/m$^2$ or $1\times 10^9$ A/m$^2$. Typically, the magnetic field for separation $H_{SEP}$ will be an order of magnitude below these upper limits. FIG. 13 is a schematic illustration of the use of various magnetic fields according to embodiments of the invention in succession in dependency of time, t. Only the numerical values of the magnetic fields are indicated as the three magnetic fields could have different direction from one another. At first a magnetic field is applied for enhancement of the agglutination process. Subsequently a magnetic field for separation of magnetic particles in dependency of size is applied. Finally, the $H_{AC}$ is applied. The magnetic field $H_{SEP}$ and magnetic field $H_{ENH}$ are indicated as being constant over time, but they could also be time-dependent, and alternating in direction like the magnetic field $H_{AC}$ for measurement of the one or more agglutination parameters.

Figure 16A:
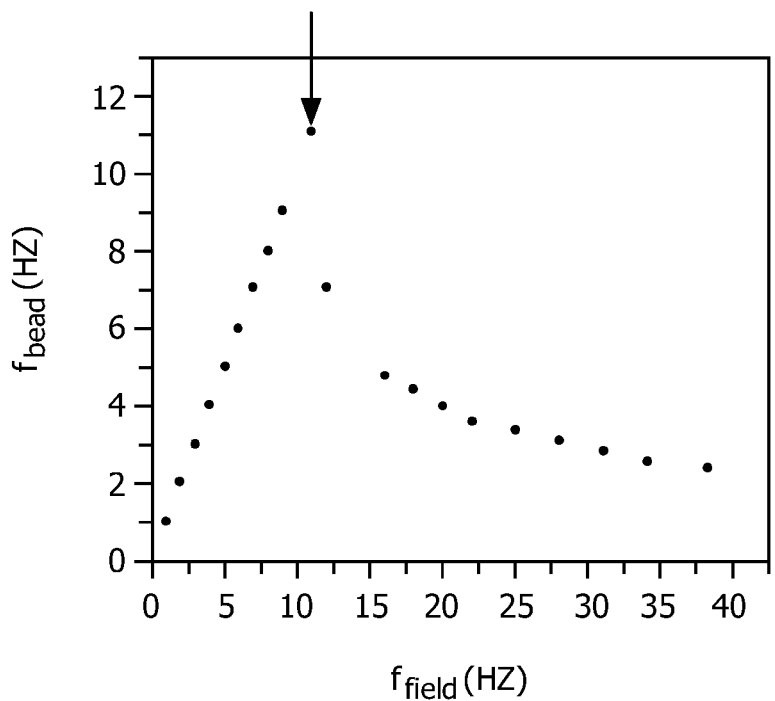
FIGS. 16a and 16b illustrates the effect of the frequency and magnitude of $H_{AC}$ on the rotation rate of a permanent magnetic particle as can be used in embodiments according to the present invention.
Figure 16B:
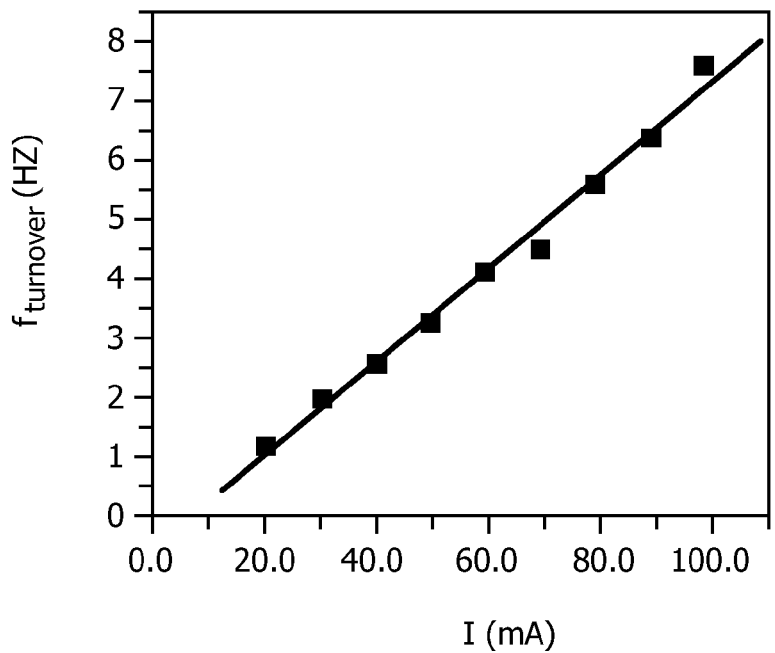
Figure 17A:
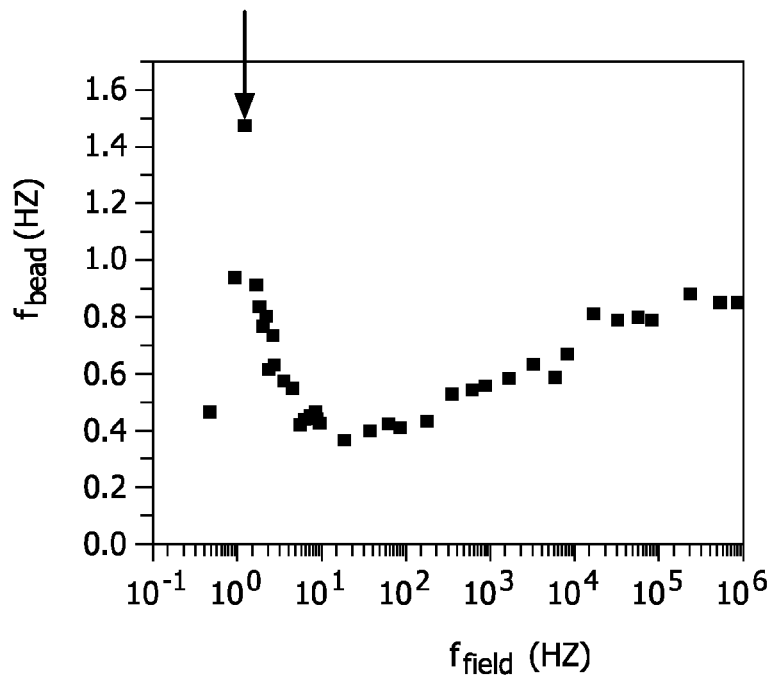
Figure 17B:
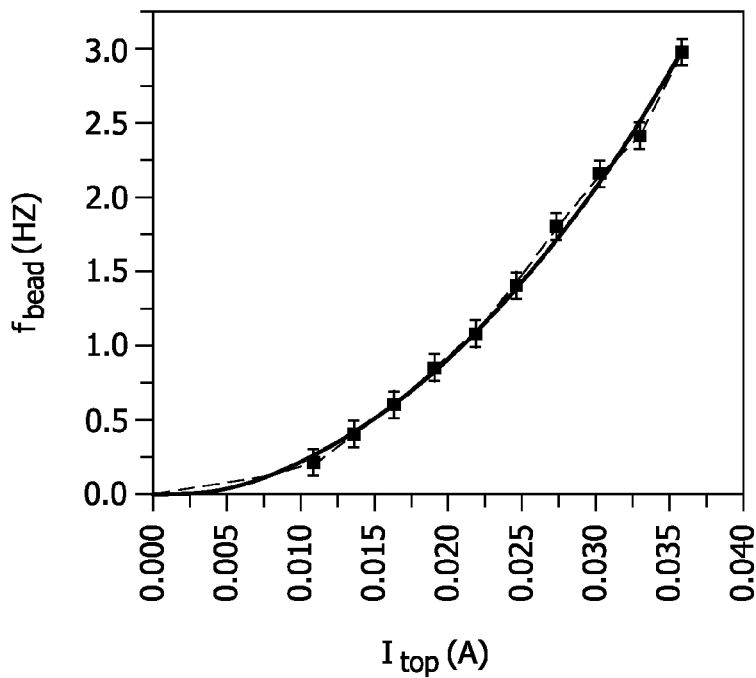
Figure 19:
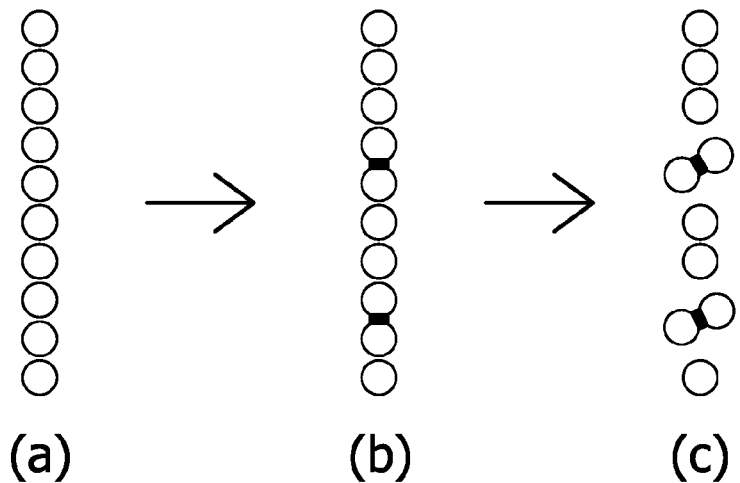
FIG. 19 is a schematic illustration of an example of an agglutination assay whereby agglutination is measured in the presence of individual beads as can be used in embodiments according to the present invention.

Another set of particular examples illustrates optional features regarding the AC magnetic field applied to the assay. FIGS. 16A to 18 illustrate, by way of example the present invention not being limited thereto, the phenomenon whereby rotation of the particles is obtained up to a given frequency, referred to as the slipping frequency and [FIG. 18, 2 peaks . . . not sure . . . ] at frequencies substantially higher than the slipping frequency. FIG. 16A shows the rotation frequency of a single magnetic particle as a function of the applied angular frequency of the rotating magnetic field. The arrow indicates the critical slipping frequency. The data shown in the example of FIGS. 16A, 16B, 17A and 17B were obtained for a magnetic particle with a diameter of 2.8 micrometer, having a large non-permanent magnetizability and a small permanent magnetization. In the example of FIG. 16A, the bottom current ($I_{bottom}$) for generating the rotating magnetic field was 0.046 Ampere (A). FIG. 16B shows the critical slipping frequency as a function of current applied to the current wires generating the rotating magnetic field. A current of 100 mA corresponds to a field of 2 mT at the position of the magnetic particle in the present example. The linear behavior indicates that the magnetic torque originates from a permanent magnetization in the magnetic particle. FIG. 17A shows the optically measured rotation frequency of the single magnetic particle as a function of applied angular frequency of a rotating magnetic field, in a wide frequency range expressed in a logarithmic scale in the X-axis. The effect of the permanent magnetization is visible in the low frequency range (lower than about 10 Hz), and the effect of the non-permanent magnetization is visible in the higher frequency range (up to about 10 MHz). FIG. 17B shows the magnetic particle rotation frequency as a function of current applied to the current wires at a frequency of 40 kHz. The quadratic behavior of the magnetic particles in the rotating magnetic field indicates that the magnetic torque originates from the susceptibility of the magnetic particle, i.e. a non-permanent magnetization. FIGS. 17 and 18 illustrate the unexpected finding wherein at frequencies higher than the critical slipping frequency, the rotation frequency of the particle increases, respectively for a single magnetic particle and a cluster of two magnetic particles. The double arrow in FIG. 18 indicates that rotation frequency of the magnetic particle under the influence of such AC magnetic field operated at a much higher frequency than the critical slipping frequency, rises to a maximum which is higher than the rotation frequency at the critical slipping frequency. The latter depends on the current, whereby at low frequencies the rotation frequency increases linear with the applied field strength while at high frequencies the rotation frequency increases quadric with the applied field strength. So above a certain field strength the critical slipping frequency is lower than the maximum achievable frequency). Preferably the agglutinated particles or magnetic particle clusters are rotated with an axis-of-rotation not coinciding with a dominant axis of magnetically formed chains of magnetic particles (see FIG. 19). In this way the clusters can be identified even in the presence of chains of individual particles.

In the absence of binding to a surface, clusters and single particles can be re-dispersed into the bulk solution after magnetophoretic separation and detection. This feature of the invention gives the method of the invention the potential for real-time monitoring of the assay, which is interesting for example in real-time nucleic-acid amplification such as PCR. Re-dispersion of clusters in the bulk solution and melting the PCR product enables re-usage of the primers on the particles which is required for exponential amplification in PCR.

It is an advantage of embodiments according to the present invention that these can make use of magnetic particles as labels and specific detection in the vicinity of a non-binding sensor surface, which enables detection of a target with low affinity, such as a low affinity binding antibody, omitting fluid wash steps.

It is an advantage of embodiments using such magnetic particles that detection can be done in raw samples. It is an advantage of embodiments using magnetic particles as in the present invention, that no fluid wash steps are required, which besides speed and ease, increases sensitivity of the assay. It is an advantage of embodiments using magnetic particles that furthermore an actuation step can be provided to increase the chance of binding.

It is an advantage of embodiments according to the present invention that no binding to the sensor surface is needed, therefore no specific sensor surface modification or derivatisation is required.

It is another aspect of the present invention to provide a kit for performing the method for measuring agglutination as described above. Such a kit comprises one or more magnetic particles for performing an agglutination assay in the presence of a specified target. The kit may further comprise the reaction chamber in which the agglutination assay is performed. The kit may also further comprise assay additives such as liquids in which the assay is performed. In particular, in the kit, the one or more magnetic particles 3, 15 and said liquid may be premixed and contained in the reaction chamber. This particular embodiment has the advantage that only the sample that needs to be tested on the presence of the target has to be added to perform the test. No further manipulation is required which can speed up the assay, and which may result in higher sensitivity and/or reproducibility of the assay.

It is also an aspect of the invention to provide a device for measuring one or more agglutination parameters in a target-induced agglutination assay. The device comprises an agglutinator means for performing an agglutination process resulting in agglutinated particles 100 which are unattached to any surface of the reaction chamber wherein the assay is kept during the measurement. The agglutinated particles comprise one or more magnetic particles. The device furthermore comprises a magnetic field generating means for applying an AC magnetic field to the assay. Such a magnetic field may be applied to the reaction chamber wherein the assay is kept such that it is felt by the assay. The assay, and thus the reaction chamber wherein the assay is kept during the measurement, may be in the vicinity of the at least one sensor element by which the effect of the applied magnetic field is to be sensed. The at least one sensor element may be based on any suitable technology for detecting the effect of the AC magnetic field on the agglutinated particles 100. It may for example be an optical detector for measuring an optical effect, a magnetic detector for measuring a magnetic effect, an electrical detector for measuring an electrical effect or an acoustic detector for measuring an acoustic effect. If a magnetic detector is used, the detector may be a Hall probe or a magnetoresistive detector element, such as for example an GMR, AMR or TMR. The at least one sensor element is arranged for measuring on the unattached agglutinated particles an effect of the AC magnetic field whereby the measured effect is indicative of the one or more agglutination parameters. In one embodiment of this aspect of the invention, the device further comprises a separation means for performing a separation process in dependency on the size of the agglutinated particle. In a particular embodiment, the separation means may be a magnetic field generator adapted for generating an inhomogeneous magnetic separation field $H_{SEP}$. The separation means may be a component having the functionality of the different separation processes as described above. In another particular embodiment, the device further may comprise a controlling means for controlling the frequency of the generated AC magnetic field to operate at a frequency substantially higher than the slipping frequency of a single magnetic particle. The frequency of the applied AC magnetic field may be at least a factor 10 larger, or at least factor 100 larger, or a at least a factor 1000 larger.

The method of embodiments of the invention can be implemented in any suitable form including hardware, software, firmware or any combination of these. The invention or some features of the invention can be implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

The device, methods and systems of embodiments of this invention are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device, methods and systems described in embodiments of the present invention can be used as rapid, robust, and easy to use point-of-care biosensors for small sample volumes. The reaction chamber can be a disposable item to be used with a compact reader, containing the one or more magnetic field generating means and one or more detection means. Also, the device, methods and systems of the present invention can be used in automated high-throughput testing. In this case, the reaction chamber is e.g. a well plate or cuvette, fitting into an automated instrument.

Agglutination assays as described for embodiments of the present invention are very suitable for high-throughput systems, such as systems with microtiterplates or vials, and flow systems (as in flow cytometry). Furthermore, cluster assays have potential for real-time monitoring of the assay, which is interesting for real-time PCR for example.

Furthermore, the device and methods of embodiments of this invention are suited for high-parallel detection of clusters. Detection of many clusters can be performed in parallel, which makes the techniques suitable for rapid and accurate measurements.

It is to be understood that although preferred embodiments, specific constructions and configurations, as well as materials, have been discussed herein for devices according to the present invention, various changes or modifications in form and detail may be made without departing from the scope of this invention as defined by the appended claims.

The invention claimed is:

1. A method for measuring agglutination of magnetic particles in a target-induced agglutination assay performed in a reaction chamber, the method comprising the acts of:
providing the magnetic particles in the assay, said magnetic particles being capable of binding to target;
performing an agglutination process resulting in agglutinated particles, comprising a least two of said magnetic particles attached together;
applying an alternating current magnetic field to the assay in the reaction chamber, and
measuring with an at least one sensor element, an effect of the alternating current magnetic field on the agglutinated particles unattached to any surface of the reaction chamber, wherein the measured effect is indicative of one or more agglutination parameters.

2. The method according to claim 1, further comprising the act of concentrating magnetic particles near a sensor surface of the at least one sensor element.

3. The method according to claim 1, further comprising the act of performing a separation process in dependency on the size of the agglutinated particles.

4. The method according to claim 3, wherein the separation process is performed by magnetic forces acting on at least a portion of the magnetic particles in the assay, said magnetic forces originating from an inhomogeneous magnetic separation field.

5. The method according to claim 4, wherein the magnetic forces applied for the separation process are different from forces generated by the alternating current magnetic field.

6. The method according to claim 3, further comprising measuring different size fractions of the agglutinated particles using a plurality of sensors resulting from said separation process.

7. The method according to claim 1, wherein said alternating current magnetic field has a frequency significantly higher than a critical slipping frequency of a single magnetic particle.

8. The method according to claim 1, wherein measuring act comprises measuring at least one of a magnetic signal, an optical signal, electrical signal, and a combination thereof.

9. The method according to claim 1, wherein the assay is positioned in proximity of a surface of the at least one sensor element.

10. The method according to claim 1, wherein a direction of the generated alternating current magnetic field is substantially parallel to a surface of the at least one sensor element.

11. The method according to claim 1, further comprising the act of applying an agglutination enhancement magnetic field for enhancing the agglutination process.

12. The method according to claim 1, wherein the effect of the alternating current magnetic field is measured over time.

13. The method according to claim 1, further comprising the act of determining a size distribution of the agglutinated particles.

14. The method according to claim 1, wherein the assay is a biochemical assay.

15. A kit for quantitatively measuring the one or more agglutination parameters of particles in the target-induced agglutination assay according to claim 1, the kit comprising the magnetic particles being capable of binding to the target.

16. The method of claim 1, wherein the magnetic particles include a first magnetic particle and a second magnetic particle, and wherein an agglutinate particle of the agglutinated particles includes both the first magnetic particle and the second magnetic particle attached together through the target bound by binding moieties.

17. A device for measuring one or more agglutination parameters of magnetic particles in a target-induced agglutination assay, the device comprising:
  an agglutinator unit configured to perform an agglutination process resulting in agglutinated particles comprising at least two magnetic particles attached together, the agglutinated particles being unattached to any surface,
  at least one sensor element; and
  magnetic field generator configured to apply an alternating current magnetic field to the assay,
  wherein the sensor element configured to measure on the unattached agglutinated particles an effect of the alternating current magnetic field on the agglutinated particles, the measured effect being indicative of the one or more agglutination parameters.

18. The device according to claim 17, further comprising a concentration unit configured to perform a concentration process of particles near a sensor surface of the sensor element independency on a size of the agglutinated particles.

19. The device according to claim 17, further comprising a controller configured to control frequency of the generated alternating current magnetic field to be significantly higher than a critical slipping frequency of a single magnetic particle.

20. The device of claim 17, further comprising a separation unit configured to perform a separation process in dependency on a size of the agglutinated particles.

* * * * *